United States Patent [19]

Sarantakis

[11] 4,282,143
[45] Aug. 4, 1981

[54] OCTAPEPTIDES LOWERING GROWTH HORMONE

[75] Inventor: Dimitrios Sarantakis, West Chester, Pa.

[73] Assignee: American Home Products Corporation, New York, N.Y.

[21] Appl. No.: 159,327

[22] Filed: Jun. 13, 1980

[51] Int. Cl.³ ............... C07C 103/52; C08L 37/00
[52] U.S. Cl. .................... 260/112.5 S; 260/8
[58] Field of Search .................... 260/112.5 S

[56] References Cited

PUBLICATIONS

Vale et al., Matabolism, 27 1391 (1978).
Veber et al., Nature 280 512 (1979).

*Primary Examiner*—Delbert R. Phillips
*Attorney, Agent, or Firm*—Richard K. Jackson

[57] ABSTRACT

Polypeptides of the formula:

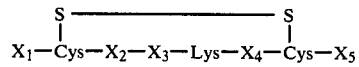

in which
$X_1$ is Phe, D-Phe or $C_6H_5CH_2CH_2CO-$;
$X_2$ is Phe, Tyr, Trp, Met or Leu;
$X_3$ is Trp or D-Trp;
$X_4$ is Thr, Val, α-Abu or Phe;
and
$X_5$ is Phe, D-Phe or $-NHCH_2CH_2C_6H_5$;

the linear precursor intermediates thereof and pharmaceutically acceptable salts and amides thereof are selective inhibitors of growth hormone release without materially altering blood serum levels of glucagon or insulin. In addition, the above-described compounds are active growth hormone suppressants for periods as long as two hours.

3 Claims, No Drawings

OCTAPEPTIDES LOWERING GROWTH HORMONE

SUMMARY OF THE INVENTION

Polypeptides of the formula:

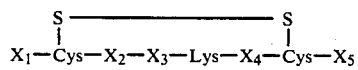

in which
- $X_1$ is Phe, D-Phe or $C_6H_5CH_2CH_2CO—$;
- $X_2$ is Phe, Tyr, Trp, Met or Leu;
- $X_3$ is Trp or D-Trp;
- $X_4$ is Thr, Val, α-Abu or Phe;

and
- $X_5$ is Phe, D-Phe or $—NHCH_2CH_2C_6H_5$;

the linear precursor intermediates thereof and pharmaceutically acceptable salts and amides thereof are selective inhibitors of growth hormone release without materially altering blood serum levels of glucagon or insulin. In addition, the above-described compounds are active growth hormone suppressants for periods as long as two hours.

DETAILED DESCRIPTION OF THE INVENTION

In accordance with this invention there is provided a group of polypeptides of the formula:

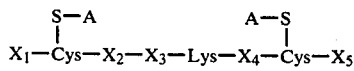

in which
- $X_1$ is Phe, D-Phe or $C_6H_3CH_2CH_2CO—$;
- $X_2$ is Phe, Tyr, Trp, Met or Leu;
- $X_3$ is Trp or D-Trp;
- $X_4$ is Thr, Val, α-Abu or Phe;
- $X_5$ is Phe, D-Phe or $—NHCH_2CH_2C_6H_5$;
- and the A groups are hydrogen or a direct bond between the two sulfur atoms;

or a pharmaceutically acceptable salt or amide thereof. These compounds, while possessing the common ability to suppress growth hormone, differ from somatostatin in their selective activity toward growth hormone without suppression of glucagon and insulin, in their long term biological activity and structurally in that they replace Ala[1]—Gly[2] with D-Phe or des-amino Phe; omit Lys[4]—Asn[5]—Phe[6]; retain Phe[7] or replace it with Tyr, Trp, Met or Leu; optionally substitute D-Trp for Trp[8]; replace Thr[10]—Phe[11]—Thr[12]—Ser[13] with Thr, Val, α-Abu or Phe; and add C-terminally Phe, D-Phe or $NHCH_2CH_2C_6H_5$. Basically, the compounds of this invention may be viewed as cyclic octapeptides containing Phe, D-Phe or des-amino Phe N-terminally and Phe, D-Phe or descarboxy Phe C-terminally. The aromatic hydrophobic terminal groups uniquely characterize the compounds of this invention and are critical for their potency and selectivity, i.e., removal of the N-terminal group deactivates the compounds of action.

The pharmaceutically acceptable salts of the compounds of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic or ascorbic acid and the like. Similarly when the C-terminal moiety is Phe or D-Phe, carboxylic acid salts of alkali metals and ammonia are produced by careful neutralization of the acid. By amides of the compounds disclosed herein, applicant intends to embrace alkyl amides containing from 1 to 4 carbon atoms, which amides are produced conventionally.

The octapeptides selectively inhibit release of growth hormone without materially altering blood levels of insulin and glucagon. As such, they are useful in treatment of acromegaly and diabetes mellitus to counteract the effects of excessive growth hormone blood levels.

The linear precursor intermediates of the cyclic octapeptides may be depicted as follows:

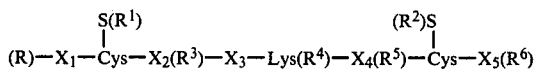

in which $X_1$, $X_2$, $X_3$ and $X_4$ are defined above and $X_5$ is Phe or D-Phe and
- $R^1$ and $R^2$ are hydrogen or a sulfhydryl protecting group;
- $R^3$ is hydrogen or a hydroxyl protecting group for Tyr;
- $R^4$ is hydrogen or a $N^\epsilon$ protecting group of Lys;
- $R^5$ is hydrogen or a hydroxyl protecting group for Thr; and
- $R^6$ is hydrogen or $—CH_2$(polystyrene resin). These intermediates comprise the fully protected and partially protected octapeptides bound to a hydroxy methylated polystyrene resin support employed in solid phase synthesis of the polypeptide as well as the fully deprotected linear polypeptide removed from the resin support.

The protecting groups employed during preparation of the linear intermediates are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (Boc), 2,2,2-trichloroethoxycarbonyl, amyloxycarbonyl, cyclopentyloxycarbonyl, cyclohexyloxycarbonyl, trityl, etc., the preferred group being tert-butyloxycarbonyl.

Examples of the sulfhydryl protecting groups $R^1$ and $R^2$ and the hydroxyl protecting group $R^3$ of tyrosyl or $R^5$ of threonyl are benzyl, p-methoxybenzyl, p-chlorobenzyl, p-nitrobenzyl, trityl, benzyloxycarbonyl, p-methoxybenzyloxycarbonyl, and the like. The p-methoxybenzyl group is preferred for protection of cysteinyl sulfur while the benzyl group is preferred for the tyrosyl and threonyl moiety.

Protecting groups for the nitrogen (ε) atom of lysine include tosyl, benzyloxycarbonyl, 2-chlorobenzyloxycarbonyl, and tert-butyloxycarbonyl, preferably the 2-chlorobenzyloxycarbonyl group.

The support employed in the solid phase synthesis of these compounds is a chloromethylated or hydroxymethylated polystyrene resin cross-linked with divinylbenzene. These resins are prepared by known methods and are commercially available in the art.

The following examples illustrate the preparation of H-Phe-Cys-Phe-D-Trp-Lys-Thr-Cys-D-Phe-OH cyclic (2–7) disulfide which is representative, in its solid phase preparation and biological activity, of the other compounds of the invention, supra.

EXAMPLE 1

N$^\alpha$-tert-Butyloxycarbonyl-L-phenylalanyl-S-p-methoxybenzyl-L-cysteinyl-L-phenylalanyl-D-tryptophyl-N$^\epsilon$-2-chlorobenzyloxycarbonyl-L-lysyl-O-benzyl-L-threonyl-S-p-methoxybenzyl-L-cysteinyl-D-phenylalanyl-oxymethyl-polystyrene ester Chloromethylated polystyrene (Lab Systems Inc.) (1.04 mequiv Cl/g) was esterified with Boc-D-Phe-OH according to Gisin, Helv. Chim, Acta., 56, 1976 (1973) and the polymeric ester (8 g.) was placed in peptide synthesizer Beckmann 990A. Program 1 was used for the incorporation of the following amino acids: Boc-Cys(SMBzl)OH, Boc-Thr(Bzl)OH, Boc-Lys(ClCBz)OH, Boc-D-Trp-OH, Boc-Phe-OH, Boc-Cys(SMBzl)OH and Boc-Phe-OH. Program 2 was employed for the completion of the coupling.

Program No. 1

Peptide Synthesizer-Beckmann 990A

1. Wash with $CH_2Cl_2 \times 3$.
2. Treat with TFA-$CH_2Cl_2$-EDT, 1:1:5% for 5 minutes.
3. Repeat (2) for 25 minutes.
4. Wash with $CH_2Cl_2 \times 4$.
5. Treat with TEA 12% in DMF for 1 minute.
6. Repeat (5) for 5 minutes.
7. Wash with $CH_2Cl_2 \times 3$.
8. Add 4 equivalents of Boc-protected amino acid and stir for 5 minutes.
9. Add 2 equivalents of 1 M-DIC solution in DMF and stir for 25 minutes.
10. Add 2 equivalents of 1 M-DIC solution in DMF and stir for 180 minutes.
11. Wash with $CH_2Cl_2 \times 3$.
12. Wash with methanol $\times 3$.
13. Wash with $CH_2Cl_2 \times 3$.

Program No. 2

Peptide Synthesizer, Beckman 990A

1. Wash with $CH_2Cl_2 \times 3$.
2. Add 2 equivalents of Boc-protected amino acid and stir for 5 minutes.
3. Add 2 equivalents of 1 M-DIC solution in DMF and stir for 180 minutes.
4. Wash with DMF $\times 3$.
5. Wash with $CH_2Cl_2 \times 3$.
6. Wash with methanol $\times 3$.
7. Wash with $CH_2Cl_2 \times 3$.

EXAMPLE 2

L-Phenylalanyl-L-cysteinyl-L-phenylalanyl-D-tryptophyl-L-lysyl-L-threonyl-L-cysteinyl-D-phenylalanine cyclic (2-7) disulfide The peptidoresin of the previous example (13 g.) was mixed with anisole (25 ml) and treated with liquid HF (200 ml) in an ice-bath and with exclusion of air, for one hour. The excess HF was removed in vacuo as fast as possible (ca. 60 minutes) and the residue was taken in 20% aqueous AcOH (100 ml) filtered and the filtrate was poured into 6 liters of deaerated water. The pH of the solution was adjusted to 6.9 with dilute $NH_4OH$ and the disulfhydryl compound was oxidized with a solution of $K_3Fe(CN)_6$ (3 g in 500 ml $H_2O$). The yellow solution was adjusted to pH 5 with glacial AcOH and treated with Bio Rad AG 3 (chloride form) for 30 minutes. The mixture was filtered and the filtrate was passed through a column of Bio Rex 70 (H$^+$ form). The peptidic material was eluted with a mixture of water-pyridine-glacial acetic acid, 66:30:4, v/v and lyophilized to yield 4 g of crude material. This material was applied onto a column of Sephadex G-25 (M) (2.5 cm $\times$ 160 cm) and eluted with 30% aqueous AcOH and the eluate collected in 5.1 ml fractions. The material which eluted in fractions 114-130 was pooled and lyophilized to yield 1.76 g. of the title compound. TLC silica gel precoated glass plates (Merck) $R_f$ (n-BuOH-water-AcOH, 4:1:1, v/v 0.47. $R_f$ (n-BuOH-water-AcOH-pyridine, 30:24:6:20, v/v) 0.77. HPLC [$C^{18}$-$\mu$ Bondapak, 4 mm $\times$ 30 cm, $CH_3CN$-$H_2O$, 2:1, v/v, 95 ml glacial AcOH and 4 ml $NH_4OH$/Pt] 96%.

Amino acid analysis: Thr (1) 1, Cys (2) 1.73, Phe (3) 3, Lys (1) 1.04, Trp (1) 0.86.

The product of the preceding examples illustrates the selective activity of the compounds of this invention for growth hormone suppression in the following standard procedure:

Albino male rats are administered Nembutal intraperitoneally at a dose of 50 milligrams per kilogram. Fifteen minutes later a subcutaneous injection of the test compound or physiological saline (control) is administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH), insulin, and glucagon by radioimmunoassay. The results of the assay are as follows:

| Compound | Dose $\mu$g/kg | Time min. | GH ng/ml | INS $\mu$U/ml | GLUN. pg/ml |
| --- | --- | --- | --- | --- | --- |
| Example 2 | 100 | 15 | 87 $\pm$ 17* | 125 $\pm$ 16+ | ND |
| Example 2 | 20 | 15 | 56 $\pm$ 9* | 239 $\pm$ 25 | ND |
| SRIF | 200 | 15 | 39 $\pm$ 15* | 124 $\pm$ 14+ | ND |
| Saline | — | 15 | 277 $\pm$ 55 | 183 $\pm$ 25 | ND |
| Example 2 | 100 | 15 | ND | 179 24 | 58 $\pm$ 13 |
| Example 2 | 20 | 15 | ND | 178 $\pm$ 20 | 55 $\pm$ 13 |
| SRIF | 200 | 15 | ND | 116 $\pm$ 7+ | 32 $\pm$ 6+ |
| Saline | — | 15 | ND | 165 $\pm$ 18 | 58 $\pm$ 8 |

*$p < 0.01$
+$p > 0.05$

The duration of activity of the product of Example 2 was as follows:

| Compound | Dose $\mu$g/kg | Time min. | GH ng/ml | INS $\mu$U/ml | GLUN. pg/ml |
| --- | --- | --- | --- | --- | --- |
| Example 2 | 1,000 | 60 | 233 $\pm$ 48* | ND | ND |
| Saline | — | 60 | 1869 $\pm$ 512 | ND | ND |
| Example 2 | 1,000 | 120 | 274 $\pm$ 51* | ND | ND |
| Saline | — | 120 | 2453 $\pm$ 627 | ND | ND |

*$p < 0.01$
+$p > 0.05$

As with administration of any therapeutic agent used in the treatment of diabetes mellitus, the compounds of this invention must be individualized for the patient under guidance and close control of the attending physician to reach optimum blood levels of growth hormone, insulin and glucagon. Doses for achieving the desired state vary with the condition of the patient, such as age, amount of endogenous insulin produced, the presence of glucagon secreting tumors, the route of administration, the duration of treatment, severity of the condition being treated, etc.

Thus, the compounds of this invention may be administered alone or in combination with insulin with or without carriers or excipients conventional to the route of administration selected, which may be oral, intravenous, subcutaneous, intramuscular, intranasal, intrarectally, etc. Suitable pharmaceutical compositions for application are apparent to those skilled in the art.

What is claimed is:

1. A compound of the formula:

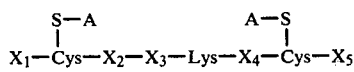

in which
$X_1$ is Phe, D-Phe or $C_6H_5CH_2CH_2CO-$;
$X_2$ is Phe, Tyr, Trp, Met or Leu;
$X_3$ is Trp or D-Trp;
$X_4$ is Thr, Val, α-Abu or Phe; and
$X_5$ is Phe, D-Phe or $-NHCH_2CH_2C_6H_5$
and the A groups are hydrogen or a direct bond between the two sulfur atoms;
or a pharmaceutically acceptable salt or amide thereof.

2. A compound of claim 1 which is

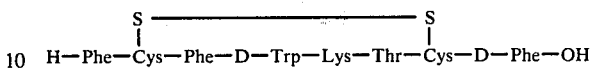

or a pharmaceutically acceptable salt thereof.

3. A compound of claim 1 which is

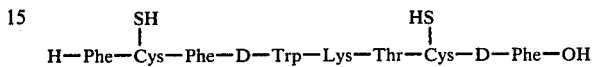

* * * * *